(12) United States Patent
Garibaldi et al.

(10) Patent No.: US 6,902,528 B1
(45) Date of Patent: Jun. 7, 2005

(54) METHOD AND APPARATUS FOR MAGNETICALLY CONTROLLING ENDOSCOPES IN BODY LUMENS AND CAVITIES

(75) Inventors: Jeffrey M. Garibaldi, St. Louis, MO (US); Walter M. Blume, Webster Groves, MO (US); Gerard H. Epplin, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 755 days.

(21) Appl. No.: 09/292,096

(22) Filed: Apr. 14, 1999

(51) Int. Cl.[7] .............................. A61B 1/01; A61B 1/00
(52) U.S. Cl. ......................... 600/118; 600/117; 600/146
(58) Field of Search ........................ 600/117, 118, 146, 600/424, 407; 128/899

(56) References Cited

U.S. PATENT DOCUMENTS

| | | | |
|---|---|---|---|
| 3,358,676 A | * | 12/1967 | Frei ........................... 600/12 |
| 5,060,632 A | * | 10/1991 | Hibino et al. ................ 600/109 |
| 5,353,807 A | | 10/1994 | DeMarco |
| 5,638,819 A | * | 6/1997 | Manwaring et al. ......... 600/117 |
| 5,681,260 A | * | 10/1997 | Ueda et al. .................. 600/114 |
| 5,876,325 A | * | 3/1999 | Mizuno et al. .............. 600/117 |
| 5,899,851 A | * | 5/1999 | Koninckx .................... 600/117 |

* cited by examiner

*Primary Examiner*—John P. Leubecker
(74) *Attorney, Agent, or Firm*—Harness Dickey & Pierce PLC

(57) ABSTRACT

A magnetically navigable endoscope system includes an endoscope having a proximal end and a distal end, the distal end having a magnetic body; a component which transmits an image, associated with the distal end; a display component for displaying the image; a magnetic field generating apparatus for generating a magnetic field to orient the magnetic body and thus the distal end of the endoscope; and a controller coordinated with the display for controlling the magnetic field generating apparatus to selectively change the magnetic field to change the orientation of the magnetic body and thus the distal end of the endoscope.

2 Claims, 2 Drawing Sheets

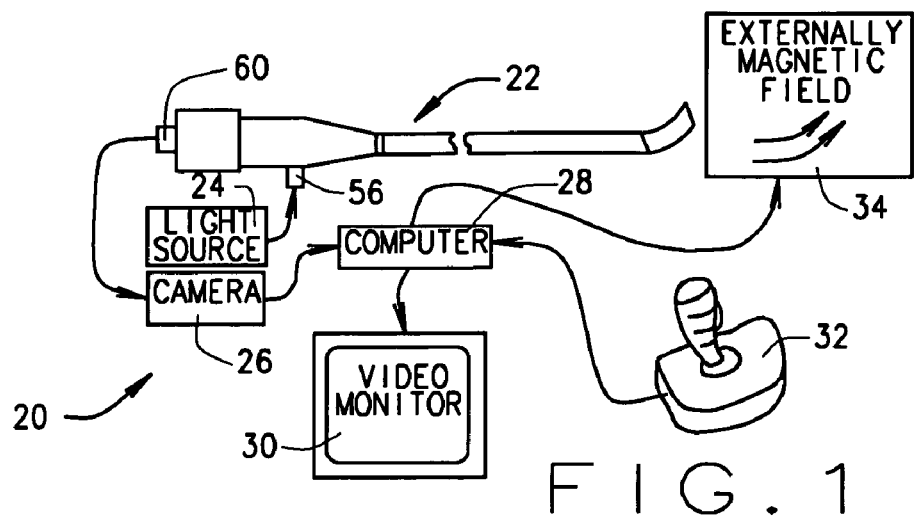
FIG. 1
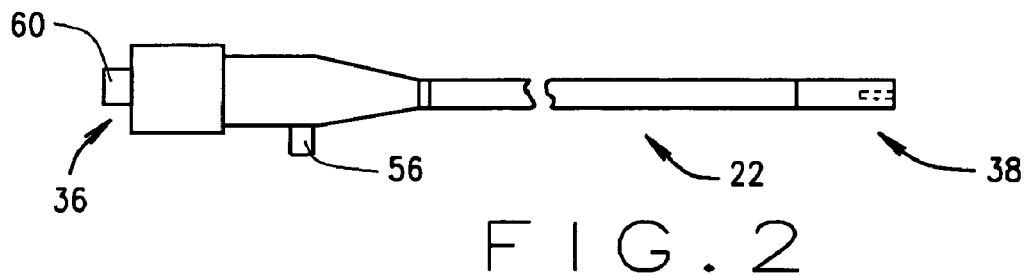
FIG. 2
FIG. 3
FIG. 4
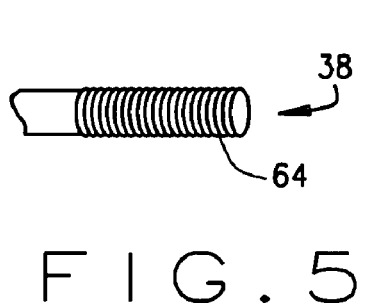
FIG. 5
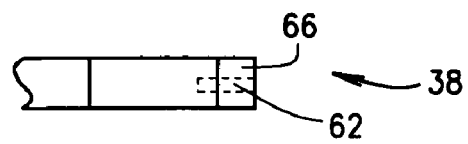
FIG. 6

METHOD AND APPARATUS FOR MAGNETICALLY CONTROLLING ENDOSCOPES IN BODY LUMENS AND CAVITIES

FIELD OF THE INVENTION

This invention relates to magnetically controlling endoscopes, and in particular to a method and apparatus for magnetically controlling endoscopes in body lumens and cavities.

BACKGROUND OF THE INVENTION

Endoscopes, which allow viewing of the interior of body lumens and cavities, are increasingly used in conducting medical procedures. One of the greatest difficulties in using endoscopes is navigating the distal end of the endoscope within the body to the procedure site. Standard endoscopes are steered using articulation wires secured to the distal end and which extend to the proximal end, where they can be operated by mechanisms incorporated in the proximal end of the endoscope. The articulation wires pull the distal end of the endoscope, causing it to articulate in the desired direction. Some endoscopes have a single plane of articulation, and navigation is affected by a combination of articulation and rotation of the endoscope. Other endoscopes have two planes of articulation, and navigation is effected by combinations of movement in the two planes. Neither of these types of endoscopes provides simple and easy omnidirectional navigation. Another problem with wire-controlled endoscopes is that the control over the movement of the tip of the endoscope diminishes with each successive bend in the endoscope, so as the endoscope is navigated through a particularly tortuous path through the body, navigation becomes increasingly difficult.

Magnetic navigation of an endoscope eliminates the difficulties encountered with mechanical navigation. A magnetic field can be generated to orient the tip of the endoscope in virtually any direction, and is not limited to movement in one or two planes. Furthermore, tip deflection is based solely on the strength of the magnetic field, and thus navigation is not affected by the path of the endoscope. However, it can be difficult for a medical professional to quickly and easily control the magnetic field in order to effectively magnetically navigate an endoscope. What has been needed is an effective way of controlling the application of magnetic fields to both orient and move magnetic devices, such as endoscopes.

SUMMARY OF THE INVENTION

The present invention provides a method and apparatus for magnetically navigating devices such as an endoscope through body lumens and cavities. Generally the magnetically navigable endoscope system of the present invention comprises an endoscope with a magnetic member, a component in the endoscope which transmits an image associated with the endoscope's distal end, a display to view the image, an input device, a computer with image processing software and a magnetic field generating apparatus for generating a magnetic field to orient the magnetic member. The endoscope construction can be similar to a standard endoscope without the articulation wires. The magnetic member is contained in the distal segment of the endoscope to orient the endoscope upon the application of an external magnetic field. The video image (e.g., a optical, ultrasound, or infrared image) from the endoscope is sent to a computer with image processing software, which provides general graphics overlays (i.e. lines and text) and image rotation functions. An input device such as a controller connected to the computer allows a physician to specify the change in deflection angle of the endoscope's distal end. As the controller is moved to the left, right, forward or backward positions, the computer senses the controller's position and accordingly processes a change in the magnetic field direction. The computer then causes the magnetic field generating apparatus to apply the new magnetic field direction.

Generally the method of magnetically navigating endoscopes of the present invention comprises specifying the direction to orient the endoscope using a variety of input devices and user interfaces, while the endoscope is manually or automatically advanced in the body lumen or cavity.

The method of the present invention can also be used in navigating the distal end of an endoscope in the bronchia; navigating the distal end of an endoscope in the brain; navigating the distal end of an endoscope in the colon and/or intestines; and navigating the distal end of the endoscope in the heart.

The endoscopes used with the method of this invention are preferably constructed to facilitate the recovery and re-integration of the image bundle, the light bundle, and the magnetics into new endoscopes, so that the endoscopes can be made disposable. Thus the entire endoscope of the present invention can be made re-usable or disposable.

The magnetically navigable endoscope system of the present invention allows a health care professional to quickly and intuitively navigate the endoscopes through body lumens and cavities. In the preferred embodiment, the system interface allows the health care professional to move the endoscope through the body without having to get involved in directly controlling the magnetic field direction and strength. This is achieved by allowing the physician to directly visualize the body lumen or cavity in which the endoscope is located, and navigate based on this viewed image.

According to the method and apparatus of this invention, the distal end of an endoscope can be oriented in virtually any direction. Moreover, the navigation is unaffected by the path of the endoscope. These and other features and advantages will be in part apparent, and in part pointed out hereinafter.

BRIEF DESCRIPTION OF THE DRAWINGS

FIG. 1 is a schematic view of an apparatus for magnetically controlling endoscopes according to the principles of this invention;

FIG. 2 is a schematic side elevation view of an endoscope for use with this invention;

FIG. 3 is a transverse cross-sectional view of the endoscope;

FIG. 4 is a side elevation view of the distal end portion of the endoscope;

FIG. 5 is a perspective view of a first alternate construction of the distal end portion of the endoscope;

FIG. 6 is a side elevation view of a second alternate construction of the distal end of the endoscope;

Corresponding reference numerals indicate corresponding parts throughout the several views of the drawings.

DETAILED DESCRIPTION OF THE INVENTION

Figure 7:
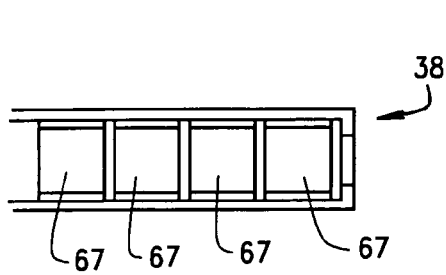
FIG. 7 is a longitudinal cross-sectional view of a third alternate construction of the distal end of the endoscope.

A system for navigating endoscopes through body lumens and cavities is indicated generally as 20 in FIG. 1. The system 20 comprises an endoscope 22, a light source 24 connected to the endoscope to provide light to illuminate the body lumen or cavity surrounding the distal end of the endoscope, an imaging device 26, for example a camera, for capturing images of the body lumen or cavity surrounding the distal end of the endoscope and a computer 28 for processing the image captured by the imaging device 26 and displaying the image on a display 30. Of course instead of a camera for capturing optical images, the imaging device could be an ultrasonic imaging device or an infrared imaging device, or some other suitable imaging device. The computer 28 is also connected to a controller, such as a controller 32, for receiving input for controlling endoscope 22, and processing the input to create an output control signal to the magnetic field generating device 34 to control the magnetic field applied to the distal end of the endoscope to move (orient and/or advance) the distal end of the endoscope in the desired direction.

The magnetic field generating device 34 is one that is capable of generating a magnetic field of selected direction and strength in an operating volume within a patient. An example of such a system is that disclosed in co-assigned, co-pending U.S. utility patent application Ser. No. 09/211, 723, field Dec. 14, 1998, entitled Open Field System for Magnetic Surgery, incorporated herein by reference. The magnetic field direction and field strength in this system can be controlled by controlling the currents applied to the electromagnetic coils comprising the system. One of ordinary skill in the art could easily implement a software algorithm to control a system which provides appropriate magnetic field direction and strength to achieve a selected orientation or movement. The magnetic field for navigating the endoscope in accordance with the present invention could also be provided with an articulated magnet, for example like that disclosed in co-assigned, co-pending U.S. Patent Application Ser. No. 60/118,959, filed Feb. 4, 1999, entitled An Efficient Permanent Magnet Means to Produce an Arbitrary Field and incorporated herein by reference.

The endoscope 22 is best shown in FIG. 2. The endoscope 22 has a proximal end 36 and a distal end 38. As shown in FIG. 3, the endoscope has a plurality of inner lumens, depending upon the application. In this preferred embodiment there are four such lumens 42, 44, 46 and 48.

The lumen 42 forms a working channel 52 extending the entire length of the endoscope 22, and providing a passage for one or more surgical instruments.

The lumen 44 forms a passage for light bundle 54 which is preferably a bundle of optical fibers extending substantially the length of the endoscope 22. The proximal end of the light bundle 54 is optically connected to a connector 56 on the side of the proximal end portion of the endoscope 22, and the distal end of the light bundle 54 terminates at the distal end 38 of the endoscope. The light source 24 is connected via connector 56 to the light bundle 54 to illuminate the area surrounding the distal end 38 of the endoscope 22. Of course, with an imaging system other than an optical system, e.g., ultrasonic or infrared imaging, the light source 24 is not necessary.

The lumen 46 forms a passage for image path 56 which, in the case of an optical imaging device 26, is preferably a bundle of optical fibers extending substantially the length of the endoscope 22. In the case of an ultrasonic or infrared imaging device 26, the imaging path 56 could be a wire or cable. The proximal end of the image path 56 is connected to a connector 60 on the distal end of the endoscope 22, and the distal end of the image bundle 56 terminates at the distal end 38 of the endoscope. The imaging device 26 is connected via connector 60 to the image path 56 to receive images from the area surrounding the distal end 38 of the endoscope 22. The imaging device 26 is in turn connected to the computer 28, which processes the image signal from the imaging device and displays in the image on the display 30.

The lumen 48 forms an optional magnet channel 60 which allows one or more magnets 62 to be positioned along the length of the endoscope 22 to permit the endoscope to be moved (oriented and/or advanced) by an applied magnetic field. The magnets could be made either of a permanent magnetic material, such as neodymium-iron-boron, or of a permeable magnetic material, such as cold rolled steel or Hiperco™. The magnets 62 are shaped to maximize their field strength for their size, and thus are typically cylindrical, and are preferably placed adjacent the distal end 38 of the endoscope 22. The distal end portion of the endoscope, showing the position of the magnet 62, is shown in FIG. 4.

The endoscope 22, and in particular the lumens 42, 44, 46, and 48, and the space surrounding the lumens 42, 44, 46, and 48, can be filled with a filler to secure the components in the endoscope. However portions of the filler along the length of the endoscope can be selectively removed by leaching to reduce the weight and stiffness of the catheter. For some applications, substantially all of the filler between the proximal and distal ends will be leached away, leaving the filler at the proximal and distal ends to hold the components in their proper orientation. It is also possible that selected portions of the filler material between the proximal and distal ends of the endoscope are leached.

The flexibility of the endoscope can vary along its length, to suit the particular function of the endoscope. In most embodiments, it is preferred that at least the distal end portion be highly flexible so that it can readily align with an applied magnetic field. For most applications, a highly flexible portion at least 3 cm long should be sufficient. The flexibility is preferably such that the distal end of the endoscope can bend at least about 120° with respect to the longitudinal axis of the immediately proximal portion of the endoscope, with a radius of curvature of about 2 cm or less.

A first alternate construction of the distal end of the endoscope is shown in FIG. 5. As shown in FIG. 5 the portion of the endoscope adjacent the distal end 38 can include a helical coil 64. The coil 64 can be made of a highly flexible permeable magnetic material to provide an alignment force of the end portion of the endoscope under an applied magnetic field. The coil 64 could also be made of a non-magnetic material to simply provide axial stiffness when the tip is arched by the magnetic field.

A second alternate construction of the distal end 38 of the endoscope 22 is shown in FIG. 6, in which the distal end of the endoscope is provided with a machined tip 66, preferably made from a permanent or permeable magnetic material. The machined tip 66 can provide the sole or additional alignment force for the tip to orient with the externally applied magnetic field.

A third alternate construction of the distal end 38 of the endoscope 22 is shown in FIG. 7, in which multiple magnet bodies are used to achieve greater magnetic torque. As shown in FIG. 7, the distal end section of the third alternate construction of the endoscope contains a plurality of magnet rings 67. The rings 67 are retained in the distal end section, and do not significantly impair the flexibility of the distal end section. The rings 67 provide sufficient magnet material so that a substantial torque can be applied to the distal end of the endoscope.

Figure 8:
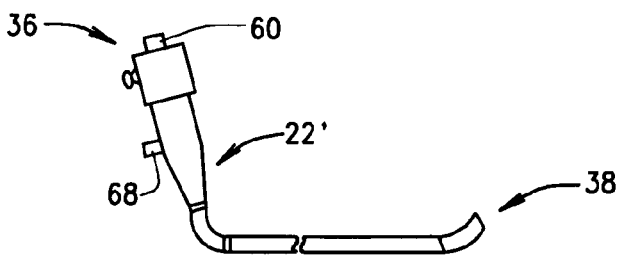
FIG. 8 is a side elevation view of an alternate endoscope construction, including an integral controller.

An alternate endoscope for use with this invention is indicated generally as 22' in FIG. 8. Endoscope 22' is similar in construction to endoscope 22, and corresponding parts are identified with corresponding reference numerals. Unlike endoscope 22, endoscope 22' includes an integral controller 68 which can be used instead of the controller 32. This allows the physician to navigate the endoscope 22' without removing his or her hands from the endoscope. The controller 68 could consist of a joystick attached to the endoscope's proximal end which the physician can manipulate to control the distal end of the endoscope. The controller 68 could alternatively consist of one or one or more sensors for sensing the orientation of the proximal end of the endoscope, and in which this sensed orientation can indicate the desired direction for the distal end of the endoscope. Thus by simply manipulating the proximal end of the endoscope, the physician can control the distal end of the endoscope.

Figure 9:
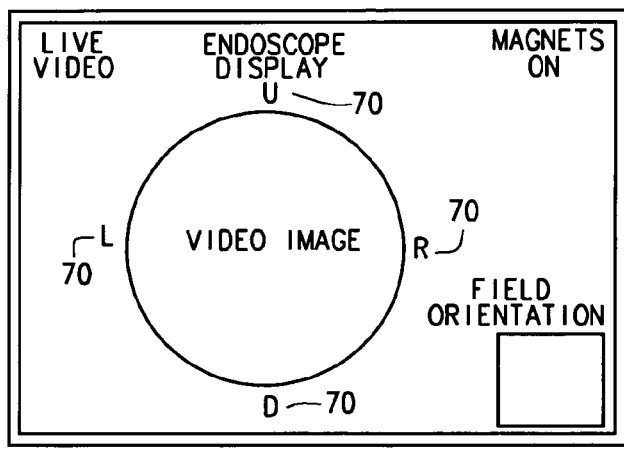
FIG. 9 is a front elevation view of a possible display for use in navigating endoscopes according to the present invention.

The computer 28 processes the image from the imaging device 26, adds an overlay, such as that shown in FIG. 9, and displays the image in an orientation intuitively coordinated with the controller 32. In this preferred embodiment, the controller and computer operate to control the externally applied magnetic field so that moving the controller left causes the magnetic field generating device 24 to change the applied magnetic field and move the distal end 38 of the endoscope 22 left as viewed on the display 30. Moving the controller 32 right causes the magnetic field generating device 24 to change the applied magnetic field and move the distal end 38 of the endoscope 22 right as viewed on the display 30. Moving the controller 32 forward causes the magnetic field generating device 24 to change the applied magnetic field and move the distal end 38 of the endoscope down as viewed on the display 30. Moving the controller 32 backward causes the magnetic field generating device 24 to change the applied magnetic field and move the distal end 38 of the endoscope 22 up as viewed on the display 30. However, these corresponding directions could be swapped, depending upon the user's preference.

To facilitate navigation it is desirable to have the display image coordinated with the controls for navigating the medical device. This can be accomplished in several different ways. The display image and the control can be periodically synchronized. The user can move the control in a preselected direction, for example, up, observe which direction the image on the display screen moves, and mark this direction on the display as the "up" direction. This marking can be conveniently done by moving a cursor or other indicator on the display with a mouse or similar input device. The user positions the cursor or other indicator to indicate the preselected direction and triggers the calibration, for example by clicking the mouse. The computer can then reprocess and reorient the image so that it is intuitively oriented with respect to the control. Alternatively one or more indicia 70, indicating the orientation of the image can be displayed on the display. The physician can use the indicia to properly operate the controller. For example, if the physician wants to move the endoscope in the direction of the "U" indicia 70, the physician moves the controller back—regardless of where the "U" indicia is actually located on the display 30. Similarly, if the physician wants to move the controller in the direction of the "R" indicia 70, the physician moves the controller to the right—regardless of where the "R" indicia is actually located on the display 30.

Another way of coordinating the display image with the controls for navigating the medical device is to provide some orientation indicator on the medical device so that the actual orientation can be determined. For example a radiopaque marker can be included on the medical device so that the orientation of the medical device can be determined visually on the display or automatically through image processing. Alternatively, some other system for remotely determining the orientation of the medical device, such as an optic sensor, a magnetic sensor, or an ultrasonic sensor can be used to obtain information about the orientation of the medical device. The computer can process the information about the orientation of the medical device and either re-orient the displayed image, or adjust the operation of the magnetic field control to intuitively coordinate the image and the operation of the control.

Of course, the image displayed on the display 30 can be oriented absolutely, i.e. so that vertical in the displayed image corresponds to actual vertical, and the controller coordinated so that the movement of the controller back moves the endoscope up, forward moves the endoscope down, and left moves the endoscope left, and right moves the endoscope right. Alternatively the image displayed on the display can be oriented relative to the control, such that regardless of the actual orientation, moving the control back moves the endoscope up as viewed on the display, moving the control forward moves the endoscope down as viewed on the display, moving the control left moves the endoscope left as viewed on the display, and moving the control right moves the endoscope right as viewed in the display.

Figure 10:
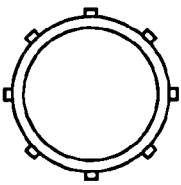
FIG. 10 is an end elevation view of the distal end of an endoscope provided with a plurality of pressure sensors around the circumference of its distal end.
Figure 11:
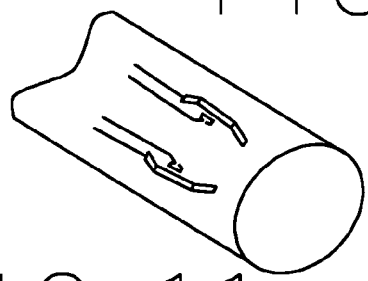
FIG. 11 is a perspective view of the distal end of the endoscope showing an exemplary construction of the pressure sensors

The magnetically navigable endoscope system of the present invention can also include one or more sensors 80, triggered by contact with an anatomical structure such as the wall of a body lumen or cavity. As shown in FIGS. 10 and 11, these sensors 80 can be distributed around the distal end of the endoscope to sense contact anywhere around the circumference of the distal end of the endoscope. The sensors may be, for example a spring contact 82 projecting from the exterior sidewall of the endoscope, resiliently biased away from contact 84, such that pressure (such as from the endoscope contacting an internal body structure such as the wall of a lumen or cavity) forces the contacts together. A controller, such as a computer, monitors the signals from the sensors and can control the magnetic field generating apparatus to selectively modify the magnetic field to change the orientation of the magnetic body such that the distal end of the endoscope remains in the desired position within the body lumen or cavity in which it is located. For example in some applications, it will be desirable that the endoscope remain substantially centered within a body lumen or cavity, to facilitate its advancement in the lumen or cavity. In other applications, it will be desirable that the endoscope remain in contact with one of the walls of the body lumen or cavity, for example for electrical mapping of the tissue or some other procedure. The system can include an advancing mechanism for advancing the endoscope, and an interlock for preventing operation of the advancing mechanism when a pre-determined number of sensors are triggered.

In a preferred mode of operation, the distal end of the endoscope is localized, for example by manually identifying the distal end of the endoscope on the displays of a bi-planar fluoroscopic imaging system. The physician can easily do this with a computer mouse or other input device, by manipulating a cursor over the end and clicking. Identifying the position of the distal end of the endoscope on two different planar images, uniquely identifies the end of the endoscope in three-dimensional space. The location of the distal end of the endoscope is then registered to a pre-operative image set such as an MR or CT image set. Once the distal end of the endoscope is registered on the pre-operative image set, the physician then identifies a direction on the preoperative image set. The magnetic field generating apparatus then generates the appropriate magnetic field to move (orient and/or advance) the distal end of the endoscope in the identified direction.

Alternatively, after the endoscope is localized, and the position registered on a pre-operative MR or CT image set, the physician could identify inputs a volume over which to move (orient and/or advance) the endoscope. This can be conveniently done by indicating the volume on a preoperative MR or CT image set. The magnetic field generating apparatus then generates the appropriate magnetic field to move (orient and/or advance) the distal end of the endoscope in the specified volume.

Figure 12:
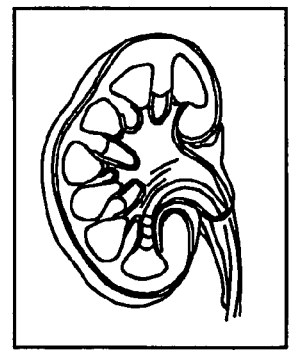
FIG. 12 is a view of the distal end of an endoscope being navigating within a kidney.

The method of the present invention can be used for navigating medical devices virtually anywhere in the body. For example the method of the present invention can be used with ureterscopes, navigating the distal end of the endoscope in the calix of the kidney, as shown in FIG. 12.

What is claimed is:

1. A magnetically navigable endoscope system comprising:

an endoscope having a proximal end and a distal end, the distal end having a magnetic body;

an imaging device which transmits an image, associated with the distal end;

a display component for displaying the image;

a magnetic field generating apparatus for generating a magnetic field to move the magnetic body and thus the distal end of the endoscope;

a controller on the endoscope, adjacent the proximal end, the controller coordinated with the display for controlling the magnetic field generating apparatus to apply a magnetic field to change the position of the magnetic body and thus the position of the distal end of the endoscope, the controller controlling the magnetic field generating apparatus to apply a magnetic field of a specific direction to change the orientation of the magnetic body and thus the orientation of the distal end of the endoscope.

2. A magnetically navigable endoscope system comprising:

an endoscope having a proximal end and a distal end, the distal end having a magnetic body;

an imaging device which transmits an image, associated with the distal end;

a display component for displaying the image, the display including indicia indicating an orientation of the displayed image;

a magnetic field generating apparatus for generating a magnetic field to move the magnetic body and thus the distal end of the endoscope;

a controller coordinated with the display for controlling the magnetic field generating apparatus to apply a magnetic field to change the position of the magnetic body and thus the position of the distal end of the endoscope, the controller controlling the magnetic field generating apparatus to apply a magnetic field of a specific direction to change the orientation of the magnetic body and thus the orientation of the distal end of the endoscope, the controller being operable in at least two mutually perpendicular directions, movement in the first direction causes the magnetic field generating apparatus to change the magnetic field to move the distal end of the endoscope in a first plane indicated in a first direction relative to the indicia, and movement in the second direction causes the magnetic field generating apparatus to change the magnetic field to move the distal end of the endoscope in a second plane, perpendicular to the first plane, indicated in a second direction relative to the indication and perpendicular to the first indicia, the indicia including at least one marker aligned with the first direction and at least one marker aligned with the second direction.

* * * * *